United States Patent
Preinitz et al.

(10) Patent No.: US 8,858,591 B2
(45) Date of Patent: Oct. 14, 2014

(54) METHOD AND DEVICE FOR SEALING A PUNCTURE HOLE IN A BODILY ORGAN

(75) Inventors: Fredrik Preinitz, Uppsala (SE); Fredrik Mahlin, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 1635 days.

(21) Appl. No.: 11/931,307

(22) Filed: Oct. 31, 2007

(65) Prior Publication Data

US 2009/0112257 A1  Apr. 30, 2009

(51) Int. Cl.
*A61B 17/08* (2006.01)
*A61D 1/00* (2006.01)
*A61B 17/00* (2006.01)

(52) U.S. Cl.
CPC ... *A61B 17/0057* (2013.01); *A61B 2017/00659* (2013.01)
USPC ........................................................ 606/213

(58) Field of Classification Search
USPC ................................ 606/213–216; 623/23.72
See application file for complete search history.

(56) References Cited

U.S. PATENT DOCUMENTS

| | | | |
|---|---|---|---|
| 5,222,974 A | 6/1993 | Kensey et al. | |
| 5,342,393 A | 8/1994 | Stack | |
| 5,350,399 A * | 9/1994 | Erlebacher et al. | 606/213 |
| 5,531,759 A * | 7/1996 | Kensey et al. | 606/213 |
| 5,593,422 A | 1/1997 | Muijs Van de Moer et al. | |
| 5,620,461 A | 4/1997 | Muijs Van De Moer et al. | |
| 6,045,569 A | 4/2000 | Kensey et al. | |
| 6,090,130 A | 7/2000 | Nash et al. | |
| 6,179,863 B1 | 1/2001 | Kensey et al. | |
| 6,508,828 B1 | 1/2003 | Akerfeldt et al. | |
| 2004/0204741 A1 | 10/2004 | Egnelov et al. | |
| 2007/0073345 A1 * | 3/2007 | Pipenhagen et al. | 606/232 |

FOREIGN PATENT DOCUMENTS

| | | |
|---|---|---|
| EP | 1 836 969 A1 | 9/2007 |
| JP | 5-212038 A | 8/1993 |
| JP | 2005-261509 A | 9/2005 |
| JP | 2006-51103 A | 2/2006 |
| WO | WO 94/28800 A1 | 12/1994 |
| WO | WO 2005/110240 A1 | 11/2005 |

OTHER PUBLICATIONS

U.S. Appl. No. 11/738,023, filed Apr. 20, 2007, Preinitz.
Japanese Office Action, Mar. 18, 2014, 4 pages.

* cited by examiner

*Primary Examiner* — Melanie Tyson
(74) *Attorney, Agent, or Firm* — Foley & Lardner LLP

(57) ABSTRACT

A method for sealing a hole in a bodily organ includes introducing a first member and a second member into the bodily organ, the first and second members being connected by an elongated member. The first and second members are retracted proximally until the first member abuts an inner surface of the bodily organ and the second member is retracted out of the hole in the bodily organ. Then, the second member is pushed distally into abutment with an outer surface of the bodily organ. A sealing device for sealing a puncture in tissue is also described.

12 Claims, 4 Drawing Sheets

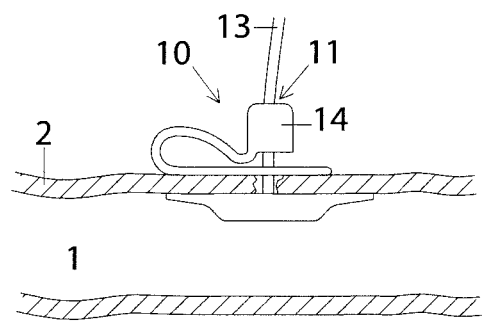
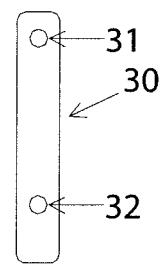
Fig. 7
Fig. 9
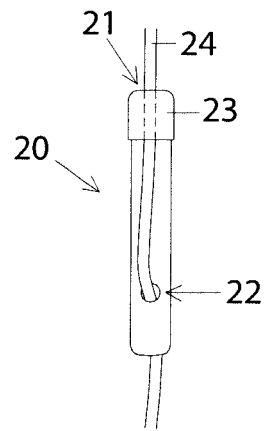
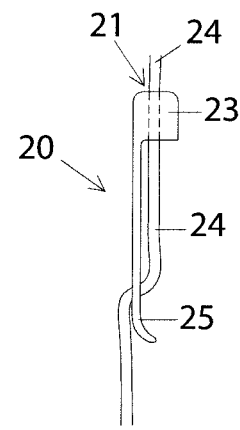
Fig. 8a
Fig. 8b
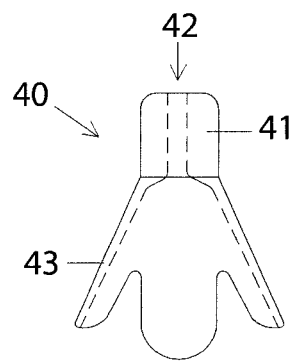
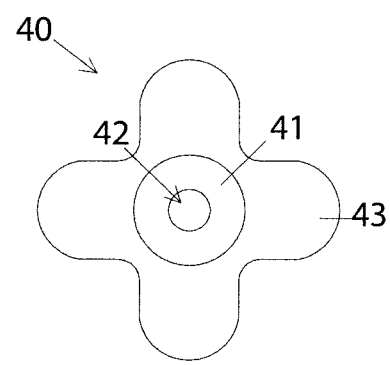
Fig. 10a
Fig. 10b

METHOD AND DEVICE FOR SEALING A PUNCTURE HOLE IN A BODILY ORGAN

FIELD OF THE INVENTION

The present invention relates generally to the field of sealing devices for the sealing of a percutaneous puncture in a vessel wall, and in particular to the class of sealing devices that comprises an intra-arterial member and an extra-arterial member, which sandwich the vessel wall and are held together by a retaining member, and more particularly to an extra-arterial member which is designed to be deployed inside the vessel and subsequently be pulled back out from the vessel and then tamped against an outer surface of the vessel wall.

BACKGROUND OF THE INVENTION

In U.S. Pat. No. 6,508,828, which is assigned to the present assignee, a sealing device is disclosed for sealing a puncture hole in a vessel wall. The sealing device comprises an inner sealing member, an outer locking member, and a retaining member. The inner sealing member is adapted to be positioned at an inner surface of the vessel wall, while the outer member is adapted to be positioned at an outer surface of the vessel wall. In use, the inner and outer members sandwich the vessel wall, and are held together by the retaining member, to thereby seal the puncture hole in the vessel wall. The entire contents of the '828 patent are incorporated herein by reference for the devices, methods and techniques described therein.

Other examples of sealing devices that comprise an inner member and an outer member, which are held together by an elongated retaining member, such as a suture or filament, can be found in, for example, U.S. Pat. Nos. 5,593,422 and 5,620,461. In U.S. Pat. No. 5,342,393, the retaining member is in the form of a stem that extends from the inner member.

In U.S. Pat. Nos. 6,179,863; 6,090,130 and 6,045,569, the outer member is in the form of a haemostatic collagen plug or sponge, by means of which it is claimed that haemostasis can be achieved within fifteen seconds.

SUMMARY OF THE INVENTION

A common feature of the known sealing devices described in the patents listed above is that the extra-arterial or outer member is designed and intended to be deployed outside of an artery; and usually the extra-arterial member is then tamped, i.e. pushed forwards, until the extra-arterial member abuts an outer surface of the artery wall. As convenient and natural that procedure may seem, it adds complexity and costs to an insertion and closure system of which the extra-arterial member is a part, because measures have to be taken to ensure that the extra-arterial member actually is correctly delivered and positioned outside of the vessel, to not jeopardize the health of a patient.

Consequently, there is still a need for an improved sealing device, which facilities the correct deployment of an outer member, and thereby provides a more user-friendly and secure sealing device.

As was stated above, known sealing devices, which comprise an inner member adapted for positioning against an inner surface of a vessel wall and an outer member adapted for positioning against a corresponding outer surface of the vessel wall, are designed such that the outer member is delivered—usually by a specially designed insertion tool—outside of the vessel wall. To, inter alia, facilitate correct deployment of the outer member, the position of the vessel wall relative to a distal end of an introducer, which is an integrated part of a corresponding insertion tool, can be detected by means of a specially designed vessel locator, such as is described in the U.S. Pat. No. 5,222,974.

Another way to ensure that a doctor does not unintentionally deliver an outer member inside a vessel is presented in the published U.S. Patent Application 2004/0204741, which is assigned to the present assignee. Here, an insertion and closure system comprises an actuator which, in a first operation mode, is configured for deployment of an inner seal inside a vessel and which, in a second mode, is configured for tamping an outer member against an outer surface of the vessel wall, wherein the actuator is arranged to be set into the second mode in response to a pulling force acting on a filament connecting the inner and outer members. The entire contents of the '741 publication are incorporated herein by reference for the devices, methods and techniques described therein.

As may be appreciated, elaborated arrangements comprising, for example, a vessel locator or an actuator having two distinguished operation modes require specially designed insertion and closure systems; and in particular an introducer sheath, which is part of such an insertion and closure system, must have a predefined length. This implies, in turn, that the insertion tool can generally not be attached to an introducer whose distal end already has been placed in a vessel, because such an introducer is usually manufactured by a manufacturer which is different from the manufacturer of the insertion and closure system, and, as there are many introducer manufacturers on the market, the length of the in-place introducer is—at least from a practical point of view—unknown. The known insertion and closure systems therefore require that an introducer, which remains after a medical operation has been performed on a patient, first is removed and then replaced by an introducer sheath which is part of the insertion and closure system in question, something which prolongs the medical operation and is accompanied by discomfort for the patient.

In contrast, the present invention introduces a novel technique for delivering an outer member which is part of a medical sealing device. The sealing device may, in turn, be part of an insertion and closure system. According to embodiments of the present invention, an outer member is deployed inside a vessel, and the outer member is then retracted until it is outside the wall of the vessel, and finally the outer member is moved forward until it abuts an outer surface of the vessel wall. By this novel approach there is neither a need to accurately locate the position of a vessel wall relative to a distal end of an introducer sheath nor to equip an insertion tool with an actuator, which must be set in a special mode before an outer member can be delivered.

In embodiments of the present invention, this novel approach is made possible by a sealing device comprising a foldable outer member, which is generally characterized by having a longitudinal axis along which a first or proximal suture hole and a second or distal suture hole have been provided. In one embodiment of the present invention, a proximal portion of an outer member has a first width equal to or less than an inner diameter of an introducer sheath, through which the outer member is to be delivered, while a distal portion of the outer member has a second width equal to or larger than the inner diameter of the introducer sheath. To ensure that the outer member can be retracted out of a puncture hole in a vessel wall, the outer member is compressible in the radial direction; and to ensure that the outer member does not have a too steep increase in dimension from the proximal width to the distal width, the ratio of distal width minus the proximal width divided by the longitudinal distance between the positions where these two widths are measured should be less than 1, and preferably less than 0.6. By this design, an outer member having a sealing function is provided.

In another embodiment, a foldable outer member has a generally elongated shape with such dimensions that no width is larger than an inner diameter of an introducer sheath. By this design, a non-sealing outer member is provided.

In embodiments of the present invention, an outer member is provided, which can be folded in the longitudinal dimension such that the first and second suture holes become essentially aligned with each other. This folding takes place when the outer member has been retracted out of a vessel. Subsequently, the outer member is tamped against an outer surface of a vessel wall. The outer member can in this doubled configuration be held in place by friction acting between a suture or filament and an inner surface of the proximal suture hole. Since an outer member according to embodiments of the invention is adapted to be deployed inside a vessel, such as an artery or a vein, or even inside some other type of bodily organ, such as a heart, the outer member should preferably be made from a non-haemostatic material, or at least from a material, which is only slightly haemostatic, to ensure that the outer member does not trigger a haemostatic reaction in blood flowing in a vessel before the outer member is retracted out of the blood vessel.

The theory behind these features will become clear from the following detailed description, but the result is that an outer member is provided which is capable of being introduced through an introducer sheath and into a vessel, subsequently retracted out of the vessel, and can then be moved forwards and finally tamped against an outer surface of the vessel wall, to thereby in co-operation with a retaining element hold an inner member in place and to, in some embodiments, also provide a sealing function. In the tamped configuration, the outer member is folded double such that a proximal suture hole is essentially aligned with a distal suture hole, while the retaining element extends through both the proximal suture hole and the distal suture hole.

BRIEF DESCRIPTION OF THE DRAWINGS

FIG. 7 shows the outer member of FIG. 6 in a final folded configuration.

FIGS. 8a and 8b show a second embodiment of an outer member according to the present invention.

FIG. 9 shows a third embodiment of an outer member according to the present invention.

FIGS. 10a and 10b show a fourth embodiment of an outer member according to the present invention.

DETAILED DESCRIPTION OF PREFERRED EMBODIMENTS

Figure 1:
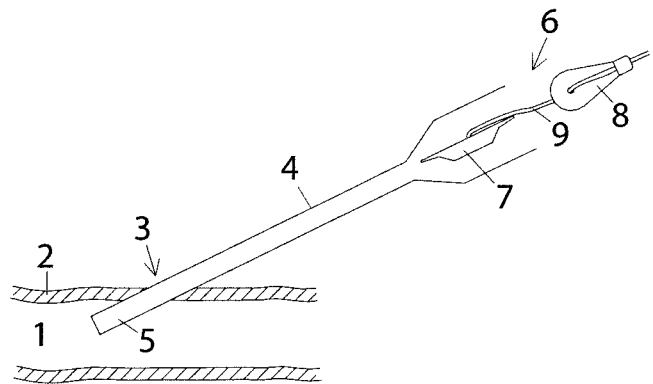
FIG. 1 illustrates schematically a first step in an insertion and sealing procedure in which a sealing device comprising an outer member according to the present invention is used.

For ease of understanding, a medical procedure in which a sealing device according to embodiments of the present invention is utilized to close a puncture hole in a vessel wall will now be described with reference to FIGS. 1 to 5, where FIG. 1 illustrates a vessel 1 surrounded by a vessel wall 2, in which a puncture hole 3 has been made. An introducer sheath 4 has previously been placed in the puncture hole 3, such that a distal end 5 of the introducer sheath 4 is inside the vessel 1. The introducer sheath 4 can be an integrated part of a dedicated insertion and closure tool, in which the sealing device has been preloaded, or the introducer sheath 4 can be a separate introducer sheath 4, to which an insertion and closure tool is attached by suitable attachments means. (One way to attach an insertion tool to an existing introducer is disclosed in the U.S. patent application Ser. No. 11/738,023, which is assigned to the present assignee and whose entire contents are incorporated herein by reference for the devices, methods and techniques described therein.) A sealing device 6 has been placed in a proximal portion of the introducer 4. The sealing device 6 comprises an inner member 7 and an outer member 8, which are connected by an elongated retaining member 9. In the present example, the elongated retaining member 9 is represented by a filament or suture 9.

Figure 2:
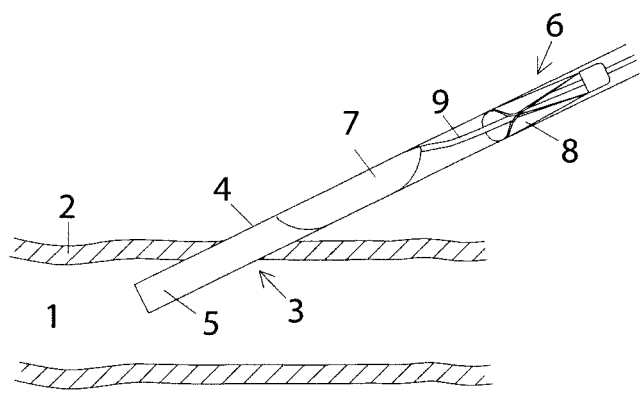
FIG. 2 illustrates schematically a second step in the insertion and sealing procedure.

In FIG. 2, the actual puncture closing procedure has commenced; and the inner member 7 as well as the outer member 8 have been moved forwards in the distal direction, and are now approximately located somewhere in the middle of the introducer sheath 4. Different kinds of actuators and actuator assemblies for moving or pushing inner and outer members of a sealing device through an introducer sheath are well-known by a person skilled in the art, and are for the sake of clarity only rudimentarily indicated in FIGS. 1 to 5. It may be noted that in this embodiment of a sealing device, both the inner member 7 and the outer member 8 are folded as they are pushed into and moved forwards in the introducer sheath 4.

Figure 3:
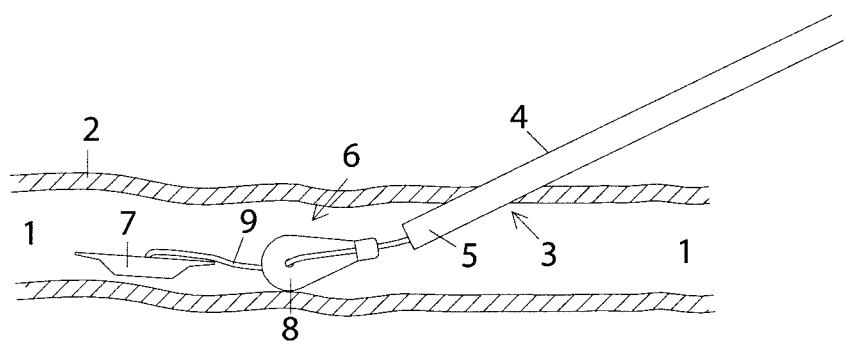
FIG. 3 illustrates schematically a third step in the insertion and sealing procedure.

FIG. 3 presents the third step of the medical procedure for closing puncture hole 3 in the vessel wall 2. In prior art, the corresponding medical protocol prescribes that an inner member is positioned within a vessel, whereas an outer member is positioned outside of the vessel wall. In the present case, both the inner member 7 and the outer member 8 are, however, deployed inside the vessel 1, as is illustrated in FIG. 3. One advantage with this method is that there is no need to accurately locate the position of the vessel wall 2 relative to the distal end 5 of the introducer sheath 4.

Figure 4:
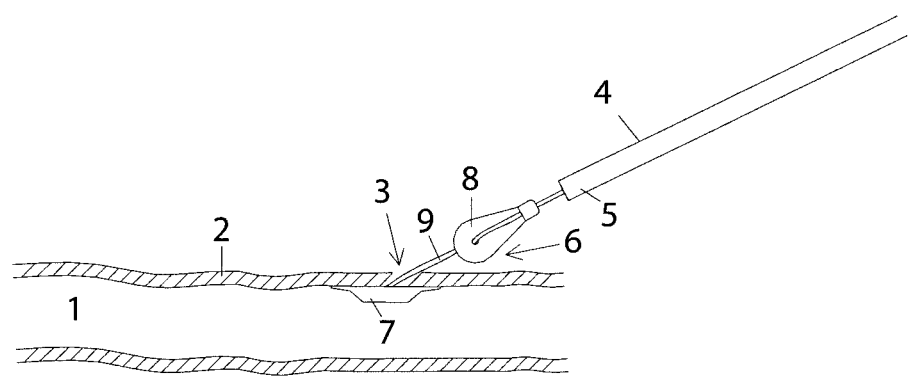
FIG. 4 illustrates schematically a fourth step in the insertion and sealing procedure.

In a fourth step of the insertion and sealing procedure, being illustrated in FIG. 4, the introducer sheath 4 is retracted, while the suture 9 is held taught, until the outer member 8 is proximally of the vessel wall 2 and the inner member 7 abuts an inner surface of the vessel wall 2. The feasibility of executing this fourth step requires that the outer member 8 is designed such that it has at least one dimension smaller than a corresponding dimension of the puncture hole 3, or, alternatively, that the outer member 8 can be compressed to a dimension smaller than a corresponding dimension of the puncture hole 3. Different embodiments of an outer member according to the present invention will be described in detail below.

Figure 5:
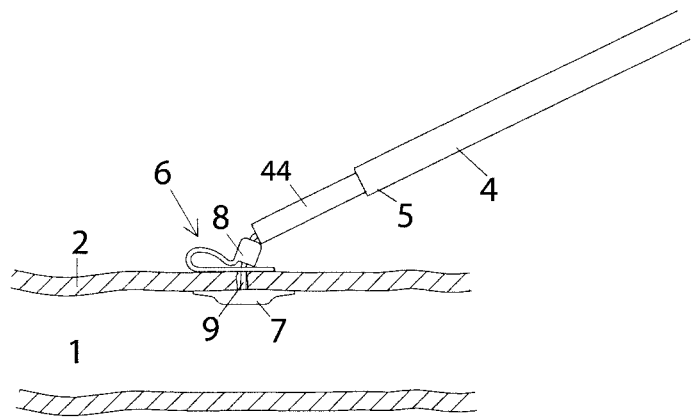
FIG. 5 illustrates schematically a fifth step in the insertion and sealing procedure.

As is illustrated in FIG. 5, the actual closing procedure ends with the outer member 8 being moved forwards and tamped against an outer surface of the vessel wall 2 by the maneuvering of a suitable actuator, a part of which is indicated in FIG. 5 and has been given reference numeral 44. It can further be seen that the outer member 8 is double-folded, such that approximately one half of a first side of the outer member 8 faces the outer surface of the vessel wall 2, while the other half of the first side faces the distal introducer end 5. In a subsequent step (not shown in FIGS. 1-5), the introducer 4 is removed and disposed, to thereby leave the sealing device 6 in place to close the puncture hole 3 in the vessel wall 2. The sealing device 6 can be held in place by a friction lock, which is created by providing the outer member 8 with a proximal hole having a nominal diameter smaller than the diameter of the suture 9.

Figure 6:
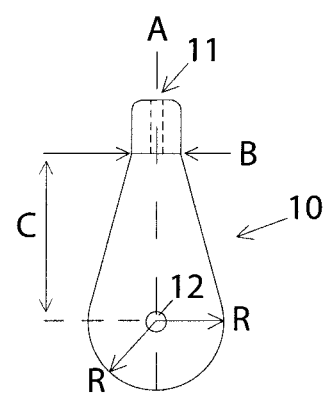
FIG. 6 shows a first embodiment of an outer member according to the present invention.

FIG. 6 shows a first embodiment of an outer member 10 according to the present invention. The outer member 10 is part of a medical sealing device, which, besides the outer member 10, also comprises an inner member, which is adapted to be positioned such that the inner member abuts an inner surface of a vessel wall, and a retaining member, which connects the inner member and the outer member 10. The novel design of an outer member according to the present invention does, in principle, not require any particular design of an inner member. That is, many different and existing types of inner members can be combined with an outer member according to the invention. However, in one embodiment of the present invention, an outer member is a non-sealing outer member, which usually requires that an inner member is a sealing inner member. In practice, it may also be necessary to modify a corresponding insertion and closure tool in such a way that it can accommodate and deliver an outer member constructed according to the teachings of the present patent specification.

Now returning to FIG. 6, it can be seen that the outer member 10 has a generally elongated shape with a longitudinal axis or dimension, being indicated by the letter A. A proximal portion of the outer member 10 is provided with a proximal or first hole 11, and has a first dimension or width B, when measured transverse to the longitudinal axis A. Since the outer member 10 is constructed to be deployed inside a vessel and then retracted out of a puncture hole in a vessel wall, the width B should be equal to or less than the corresponding dimension of a puncture hole. As the puncture hole is created, or rather sustained, by an introducer sheath, this dimension of the puncture hole would correspond to the outer diameter of the introducer sheath. The tissue of a vessel wall possesses, however, some elasticity, and it is therefore adequate to let the dimension B be equal to or less than the inner diameter of the introducer sheath. From a practical point of view this is also an advantage, because introducers are—as is well-known in the art—classified according to the size of their inner diameter. Standard sizes of introducer sheaths range from about 3 to 10 French (1 mm to 3.3 mm).

Still with reference to FIG. 6, it can be seen that the outer member 10 is provided with a second or distal hole 12, and also has a second dimension or radius R, when measured from the centre of the distal hole 12. In this exemplifying embodiment, the outer member 10 is designed to have a sealing function, which implies that the sum of two opposing radii R should be equal to or larger than two times the diameter of the puncture hole. The factor of two derives from a desire to ensure proper sealing also at maximum misalignment between the outer member and the puncture hole, i.e. when the distal suture hole is located at the periphery of the puncture hole. Applying the same reasoning as presented above, it is, however, sufficient that the sum of two opposing radii R is equal to or larger than two times the inner diameter of the introducer sheath that during the foregoing procedure was placed in the puncture hole.

From the discussion above it should be clear that the distal portion of the outer member 10, when in the state depicted in FIG. 6, nominally is larger than a puncture hole. In this embodiment, the outer member 10 is therefore compressible, such that when the outer member 10 is retracted in the proximal direction, the distal portion of the outer member 10 is compressed to a dimension smaller than the puncture hole, and the outer member 10 can be drawn out of a vessel. The compressibility of the outer member 10 is preferably accomplished by a suitable design in combination with a smooth material, e.g., soft wings outside of a harder central core, or a generally wedge or drop shaped body made from a pliable material, which deforms when the outer member is retracted out of a puncture hole. To facilitate a smooth retraction of an outer member, the transverse dimension from a proximal portion to a distal portion should not increase too steeply. For the embodiment illustrated in FIG. 6 it may therefore be suitable that two times the radius R, when measured transverse to the longitudinal axis A, minus the proximal dimension B divided by the distance C, which is the distance between the distal hole and the position where the proximal dimension B is measured, is less than or equal to 1 (and preferably less than 0.6).

$$\frac{2R-B}{C} \leq 1.0 \quad (1)$$

In the Equation 1 above, it should be clear that the factor of 1 (or 0.6) only should serve as a guideline and an indication that a too fast increasing transverse width of an outer member is not recommended. A person skilled in the art can, however, find suitable dimensions taking into account, for example, the characteristics of the materials from which the outer member is made and the characteristics of the tissue near the puncture.

As can be appreciated—in particular in conjunction with FIGS. 4 and 5—when the outer member has been retracted to a position proximally of a vessel wall, the distal portion of the outer member expands to a size larger than the puncture hole; and when the outer member subsequently is pushed forwards and ultimately tamped against an outer surface of the vessel wall, an intermediate portion, being located somewhere between the proximal portion and the distal portion of the outer member, flexes such that the outer member 10 becomes folded double. This double-folded configuration is shown in FIG. 7.

In the double-folded state illustrated in FIG. 7, the outer member 10 is held in place by friction acting between the peripheral surface of a proximal suture hole 11 and a suture 13. In other words, the proximal suture hole 11 should have a diameter smaller than the diameter of the suture 13 to create a positive fixating friction joint. In other embodiments of the invention, an outer member could also be held in place by a separate member, such as a small ring or a suture knot, which can be pushed along a suture until this separate member abuts a proximal suture hole in the outer member. To create a secure and reliable friction joint between the outer member 10 and the suture 13, the thickness of the proximal suture hole 11 (or rather the thickness of the wall surrounding the proximal suture hole) should not be too small. For that reason it can in FIGS. 1 to 7 be noted that the outer member 10 in its proximal end is provided with a collar 14, through which the proximal suture hole 11 extends. The collar 14 and the suture hole 11 therein are thus directed along the longitudinal axis A of the outer member 10. In another embodiment of the invention it is however conceivable that a proximal suture hole extends through the body of an outer member, i.e. the suture hole extends transverse to a longitudinal axis. Such a configuration is in particular feasible if the outer member is provided with a thicker central core, such that enough wall material is provided to create a positive friction joint between the peripheral wall of the proximal hole and a suture. It would also be possible to hold an outer member in place at a vessel wall by means of an elaborated way of tying a suture to thereby fixate the outer member in a double-folded configuration.

As may already have been appreciated from the above, an outer member according to the invention can be foldable and/or compressible. Herein, the term "foldable" is reserved for describing a folding of the outer member in its longitudinal direction, whereas the term "compressible" is meant to define a size reduction in the radial (or transverse) direction of the outer member. The term compressible should not be literally interpreted, but encompasses all kind of measures, such as folding, winding and compression, that reduce the radial dimension of an outer member such that it can be retracted out of a hole in a tissue wall.

A second embodiment of an outer member is illustrated in FIGS. 8a and 8b, wherein an outer member 20 is provided with a proximal suture hole 21 and a distal suture hole 22. Suture hole 21 is in this example provided in a collar 23, such that a suture 24 extends along the longitudinal axis of the outer member 20. Further, the outer member 20 has a uniform width, which should be less than or equal to the diameter of a puncture hole in a vessel wall, or, and more preferably, less than or equal to the inner diameter of an introducer sheath used to introduce the outer member 20, in accordance with the discussion above. In FIG. 8b it is further illustrated that a very distal portion 25 of the outer member 20 has been given a curved shape, such that the distal portion 25 is bent out from the longitudinal axis of the outer member 20. With this curved shape it is ensured that the outer member 20 during the tamping phase, when the outer member 20 is pushed forwards into contact with an outer surface of a vessel wall, is stopped against the outer surface and is subsequently tamped into a double-folded configuration, as is illustrated in FIG. 7 in conjunction with description of the first embodiment of an outer member according to the present invention. In this state, the outer member is arranged to have a second dimension that spans across the hole, enabling sealing of the puncture hole by at least one of the inner member and the outer member when in the locked position Without this outwardly bent shape, there would, at least theoretically, be a risk that the outer member 20 during the tamping step is pushed back into the vessel instead of abutting the outer vessel wall. Further, the outer member 20 is foldable such that a double-folded configuration can be achieved, as already has been described with reference to the outer member 10. In contrast to the previously discussed outer member 10, the outer member 20 is however not compressible in any appreciable degree, because the width of the outer member is small enough to be retracted through a puncture hole in a vessel wall without any compression. The small width implies on the other hand, that a corresponding inner member must possess a sealing capacity.

It has previously been indicated that an outer member according to the present invention can have different shapes, e.g. when it comes to how a proximal suture hole is arranged. In FIG. 9 it is illustrated that a proximal puncture hole 31 can be made perpendicular to the main body of an outer member 30. In other words, in this embodiment there is no collar provided, and certain care must be taken such that a positive fixation of the outer member 30 is achieved. By providing the outer member 30 with a thick core, such that there is enough material present to ensure a secure friction joint, this fixation can be accomplished. Another alternative is to provide a separate member, e.g. a ring-shaped disc or a knot, which along a suture or filament is slidable into abutment with the outer member 30.

The previously described embodiments have all been foldable outer members. In FIGS. 10a and 10b another type of outer member according to the invention is illustrated. Here an outer member 40 comprises a proximal cylindrical collar 41, in which a bore 42 has been made. The extension of the bore 42 coincides with a longitudinal axis of the outer member 40, such that a suture or filament (not shown in FIGS. 10a and 10b) can be threaded through the bore 42. Four (4) wings 43 extend in the distal direction from the collar 41, to give the outer member 40 the general shape of a truncated cone whose mantle has been broken up into four separate wings. In other embodiments the number of wings can be different from four.

In use, the outer member 40 is deployed inside a vessel; and when the outer member 40 is retracted out from a puncture hole made in a vessel wall, the wings 43, which preferably are made from a resilient material, compress to a smaller radial dimension. When the outer member 40 subsequently is tamped and pushed into contact with an outer surface of the vessel wall, the wings 43 are spread out, to thereby prevent that the outer member 40 is pushed back into the vessel.

Figure 11:
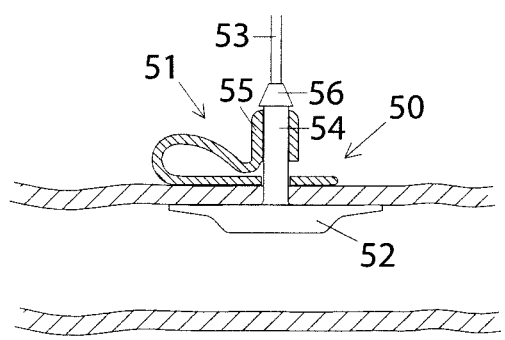
FIG. 11 shows another embodiment of a sealing device including a fifth embodiment of an outer member according to the present invention.

FIG. 11 illustrates a sealing device 50, which comprises an outer member 51 and an inner member 52, to which an elongated retaining member 53, e.g. a suture, is connected. The inner member 52 is further provided with a shaft 54, which in the locked sealing state illustrated in FIG. 11 protrudes in a collar 55 provided at a proximal portion of the outer member 51. The outer member 51 has the same general design as the outer member 10 illustrated in e.g. FIG. 6, but in the embodiment of FIG. 11, the outer member 51 and the inner member 52 are held together by friction action between the shaft 54 and an inner surface of the collar 55. To further ensure a secure locking of the outer member 51 and the inner member 52, the shaft 54 is provided with an end cap 56, which has the general shape of a truncated cone, such that the collar 55 easily can be threaded over the end cap 56, but it is impossible or at least very difficult to pass the collar 55 back over the end cap 56 once in the locked configuration shown in FIG. 11. As an alternative, a shaft could instead be provided at the outer member.

Although the present invention has been described with reference to specific embodiments, it will be apparent for those skilled in the art that many variations and modifications can be done within the scope of the invention as described in the specification and defined with reference to the claims below. It should in particular be noted that although the invention has been described in conjunction with the sealing of a vessel, such as an artery or a vein, it is also possible to apply the invention in other bodily organs, such as in the heart.

What is claimed is:

1. A device for sealing a puncture hole in a bodily organ, the device comprising:
   an inner member adapted for positioning against an inner surface of the bodily organ;
   an outer member adapted for positioning against a corresponding outer surface of the bodily organ; and
   an elongated retaining member;
   wherein the inner member is arranged at a distal end of the elongated retaining member and the outer member is movable along the elongated retaining member,
   wherein the outer member in a first state is arranged to have a first dimension enabling, after having been deployed inside the bodily organ through the puncture hole, retraction of the outer member out of the puncture hole, wherein the outer member has a compressible and resilient structure such that the outer member is reducible in size in a radial direction of the outer member when in the first state, wherein the outer member is arranged to be engaged in a locking arrangement with the elongated retaining member such that the outer member can be moved distally along the elongated retaining member and fixed in a locked position at the outer surface of the bodily organ, wherein the outer member in a second state is arranged to have a second dimension enabling sealing of the puncture hole by at least one of the inner member and the outer member when in the locked position, wherein the outer member has a first through-hole and a second through-hole, wherein the elongated retaining member passes through the first and second through-holes, and wherein, when in an undeformed condition, the outer member has the first through-hole extending in a longitudinal direction and the second through-hole extending in a direction perpendicular to the longitudinal direction.

2. A device as set forth in claim 1, wherein the outer member is substantially free of haemostatic material.

3. A device as set forth in claim 1, wherein the first through-hole is disposed at a proximal end of the outer member and the second through-hole is disposed at a distal end of the outer member.

4. A device as set forth in claim 1, wherein an outer profile of the outer member gradually increases along a length of the outer member from a proximal end of the outer member to a distal end of the outer member.

5. A device as set forth in claim 1, wherein the outer member is configured to fold onto itself.

6. A device as set forth in claim 1, wherein the outer member includes an angled portion configured to assist in folding the outer member.

7. A device for sealing a puncture hole in a bodily organ, the device comprising:
- an inner member adapted for positioning against an inner surface of the bodily organ;
- an outer member adapted for positioning against a corresponding outer surface of the bodily organ; and
- an elongated retaining member, wherein the inner member is arranged at a distal end of the elongated retaining member and the outer member is movable along the elongated retaining member, wherein the outer member has a compressible and resilient structure such that the outer member is reducible in size in a radial direction of the outer member, thereby enabling, after having been deployed inside the bodily organ through the puncture hole, retraction of the outer member out of the puncture hole, wherein the outer member is arranged to be engaged in a locking arrangement with the elongated retaining member such that the outer member can be moved distally along the elongated retaining member and fixed in a locked position at the outer surface of the bodily organ to thereby enable sealing of the puncture hole by at least one of the inner member and the outer member, wherein the outer member has a first through-hole and a second through-hole, wherein the elongated retaining member passes through the first and second through-holes, and wherein, when in an undeformed condition, the outer member has the first through-hole extending in a longitudinal direction and the second through-hole extending in a direction perpendicular to the longitudinal direction.

8. A device as set forth in claim 7, wherein the outer member includes an angled portion configured to assist in folding the outer member.

9. A device as set forth in claim 7, wherein the outer member is substantially free of haemostatic material.

10. A device as set forth in claim 7, wherein the first through-hole is disposed at a proximal end of the outer member and the second through-hole is disposed at a distal end of the outer member.

11. A device as set forth in claim 7, wherein an outer profile of the outer member gradually increases along a length of the outer member from a proximal end of the outer member to a distal end of the outer member.

12. A device as set forth in claim 7, wherein the outer member is configured to fold onto itself.

\* \* \* \* \*